(12) United States Patent
Tavernier et al.

(10) Patent No.: US 11,542,463 B2
(45) Date of Patent: Jan. 3, 2023

(54) MICRO ALGAE HARVESTING METHODS AND DEVICES

(71) Applicant: Universiteit Antwerpen, Antwerp (BE)

(72) Inventors: Serge Martin Fernand Tavernier, Lint (BE); Boris Marie Gabriel Artemieff, Sint-Lambrechts-Woluwe (BE)

(73) Assignee: Universiteit Antwerpen, Antwerp (BE)

( * ) Notice: Subject to any disclaimer, the term of this patent is extended or adjusted under 35 U.S.C. 154(b) by 620 days.

(21) Appl. No.: 16/500,675

(22) PCT Filed: Apr. 13, 2018

(86) PCT No.: PCT/EP2018/059502
§ 371 (c)(1),
(2) Date: Oct. 3, 2019

(87) PCT Pub. No.: WO2018/189361
PCT Pub. Date: Oct. 18, 2018

(65) Prior Publication Data
US 2020/0063084 A1 Feb. 27, 2020

(30) Foreign Application Priority Data

Apr. 13, 2017 (EP) ..................................... 17166645

(51) Int. Cl.
*C12M 1/26* (2006.01)
*C12M 1/12* (2006.01)
(Continued)

(52) U.S. Cl.
CPC .............. *C12M 33/14* (2013.01); *B01D 29/86* (2013.01); *B01D 63/06* (2013.01); *B01D 65/02* (2013.01);
(Continued)

(58) Field of Classification Search
None
See application file for complete search history.

(56) References Cited

U.S. PATENT DOCUMENTS

| 4,402,103 A | 9/1983 | Yanagawa et al. |
| 9,487,748 B2 | 11/2016 | Lancaster et al. |

(Continued)

FOREIGN PATENT DOCUMENTS

| CN | 202968549 U | 6/2013 | |
| CN | 106986465 A | * 7/2017 | ............ C02F 3/34 |

OTHER PUBLICATIONS

Cerda et al., Magnetic responsive brushes under flow in strongly confided slits: external field control of brush structure and flowing particle mixture separation, Royal Society of Chemistry, Soft Matter, 2019, 15, 8982, PP8982-8991. (Year: 2019).*

(Continued)

*Primary Examiner* — David C Mellon
(74) *Attorney, Agent, or Firm* — Amster, Rothstein & Ebenstein LLP

(57) ABSTRACT

The present invention relates to a particulate material separation assembly. It comprises a filtration membrane and an antifouling device. The antifouling device comprises one or more magnets and a plurality of magnetisable particles. The one or more magnets cause the plurality of magnetisable particles to self-assemble into dynamic bristles, thereby forming a brush. The particulate material separation assembly is particularly useful in the context of micro algae harvesting.

19 Claims, 12 Drawing Sheets

(51) Int. Cl.
  *C12M 3/04* (2006.01)
  *B01D 29/86* (2006.01)
  *B01D 63/06* (2006.01)
  *B01D 65/02* (2006.01)
  *C12M 1/00* (2006.01)

(52) U.S. Cl.
  CPC ............ *C12M 23/06* (2013.01); *C12M 25/16* (2013.01); *C12M 27/10* (2013.01); *C12M 39/00* (2013.01); *C12M 45/07* (2013.01); *B01D 2321/24* (2013.01); *B01D 2321/30* (2013.01)

(56) References Cited

U.S. PATENT DOCUMENTS

2008/0237098 A1    10/2008  Saho et al.
2016/0122705 A1*    5/2016  Lancaster .............. C12M 43/00
                                                        435/257.1

OTHER PUBLICATIONS

Huang et al., Magnetorheological brush—a soft structure with highly tuneable stiffness, Soft Matter, 2014, 10, 1537, PP1537-1543. (Year: 2014).*
PCT International Search Report and Written Opinion dated Aug. 9, 2018 in connection with PCT International Application No. PCT/EP2018/059502.

* cited by examiner a)

b)

a)

b)

c)

d)

MICRO ALGAE HARVESTING METHODS AND DEVICES

TECHNICAL FIELD

The present invention relates to filtration devices and methods, in particular to devices and methods for counteracting filter fouling during filtration. The present devices and methods are highly useful in the field of micro algae harvesting.

BACKGROUND

There is significant interest in algae growth as algae allow fixating $CO_2$, and/or transforming $CO_2$ in useful compounds using (sun) light as an energy source using photosynthesis. Such useful compounds include sugars, fats, nutritional compounds such as poly-unsaturated fatty acids, carotene, anti-oxidants, aquaculture feeds for e.g. fish larvae, and biomass for energy production. Also, Algae grow fast while not requiring prime agricultural soil for growth.

However, state-of-the-art algae growth systems suffer from a number of downsides. So-called open pond systems suffer from contamination problems whereas closed photo bioreactors tend to be dependent on artificial light which results in high energy costs. One solution could be the use of hybrid systems which are closed and which are based on solar energy. Another challenge is related to harvesting algae in low density growth cultures in a simple and cost-efficient way, preferably without damaging the algae. A last set of challenges is related to down-stream processing such as drying, extraction etc.

Several methods of harvesting micro algae exist: sedimentation, flotation, centrifugation, filtration, capillary dewatering, and combinations thereof. Optionally, chemical additives such as flotation or flocculation compounds may be added for increasing the efficacy of these separation processes.

Algae comprise a considerable amount of water. Accordingly the density difference between algae and growth media may be small. For fat-containing algae, the density difference can even be zero. This small or zero density difference combined with the small dimensions of algae results in spontaneous sedimentation and decantation, or flotation, to be unrealistic.

In case the algae and growth medium have a near-zero density difference, the separation efficacy can be improved by means of centrifugation at high angular velocity. However, this requires a lot of energy because a large amount of water needs to be accelerated for harvesting a relatively low amount of algae due to the low algae densities involved. In addition, associated compression may result in algae damage.

An alternative separation process is separation based on size, i.e. filtration. Dead end filtration can be difficult: once an algae-based filter cake is formed, the filter is clogged. Algae are soft, and can produce large amounts of slimy polysaccharides, and both easily form a filtration barrier, even at very thin filter cake thicknesses.

An alternative to dead end filtration is cross-flow filtration wherein an attempt is made to prevent filter cake formation by means of sideways flow. However, the sideways flow velocity should be high, implying that this comes at the cost of significant energy expenditure for pumping and it does not prevent filter cake formation altogether either. The filter cake may be removed by means of a back flush.

Another option is vibration-assisted dead end filtration in which vibration is used for creating local sideways flow, however this costs plenty of vibrational energy.

An alternative is mechanical scraping, as is done in e.g. baker's yeast preparation. In such processes a pre-formed filter bed, e.g. consisting of starch grains, is commonly used instead of a filter. The pre-formed filter bed is scraped off together with the filter cake. This process of mechanical scraping is very difficult because of the extremely high mechanical demands posed on the blade in terms of straightness, precision, etc. In addition, the filter bed material may be contaminated. Also, mechanical damage of algae during scraping is likely.

Additives may be used to avoid formation of the filter cake but this has the disadvantage that the harvested algae are no longer pure, and that the growth medium contains additives which compromises its reusability.

Accordingly, there is a need for a simple, energy-efficient device and process for cleaning a filter during use to avoid cake formation. Such a process and device should ideally allow the efficient harvesting of algae and should not result in algae damage or in growth medium or algae contamination.

SUMMARY

It is an object of the present invention to provide devices and methods for efficiently filtering particles from suspensions.

A further object of the present invention is to provide devices and methods for harvesting algae in low density growth cultures in a simple and cost-efficient way. The present devices and methods are particularly useful for harvesting micro algae, which can have sizes between 2 μm and 200 μm.

Accordingly, provided herein is a particulate material separation assembly comprising: a filter comprising a filtration membrane; and an antifouling device comprising a magnetic brush. The magnetic brush used in the context of the present invention comprises magnets and oblong features which are subjected to the magnetic field of said magnets The particular material separation assembly provided herein is further characterized in that the filter and at least a part of the antifouling device are arranged to be moveable with respect to each other such that the oblong features are capable of brushing against the filtration membrane.

In particular embodiments, the oblong features are formed by a plurality of magnetisable particles but alternative structures are also described herein. According to particular embodiments, the invention thus provides a particulate material separation assembly comprising a filter comprising a filtration membrane and an antifouling device, which antifouling device comprises a magnetic brush, wherein the magnetic brush comprises one or more magnets and a plurality of magnetisable particles, the plurality of magnetisable particles being arranged in a plurality of dynamic bristles. In this embodiment, the particular material separation assembly provided herein is further characterized in that the filter and the antifouling device are arranged to be moveable with respect to each other such that the dynamic bristles are capable of brushing against the filtration membrane.

In particular embodiments, only a part of the antifouling device is moveably disposed with respect to the filter, or the filter is moveably disposed with respect to the part of the antifouling device. Specifically when the antifouling device comprises magnetisable particles, one or more magnets, and one or more further components, the magnetisable particles and the one or more magnets on the one hand and the filter on the other hand may be moveably disposed with respect to each other whereas the one or more further components of the antifouling device remain stationary with respect to the filter.

In particular embodiments, the antifouling device comprises a cylindrical hull, wherein the one or more magnets are fixed within the cylindrical hull, wherein the cylindrical hull is coupled to a rotary actuator for rotating the cylindrical hull around its longitudinal axis, and wherein the plurality of magnetisable particles is disposed outside of the cylindrical hull.

In particular embodiments, the cylindrical hull is a first cylindrical hull positioned within a second cylindrical hull which is arranged to remain stationary during rotation of the first cylindrical hull, and said plurality of magnetisable particles is disposed outside of the second cylindrical hull.

In particular embodiments, the one or more magnets have a magnetic dipole moment which is aligned along a radial direction of the cylindrical hull.

In particular embodiments, the magnetic dipole moment of one or more magnets has a radial orientation opposite to that of circumferentially adjacent magnets. Preferably, the magnetic dipole moment of every magnet has a radial orientation opposite to that of circumferentially adjacent magnets.

In particular embodiments, the magnetic dipole moment of one or more magnets has a radial orientation identical to that of circumferentially adjacent magnets. Preferably, the magnetic dipole moment of every magnet has a radial orientation identical to that of circumferentially adjacent magnets.

In particular embodiments, the one or more magnets comprise at least four magnets. The at least four magnets are arranged in a Halbach array.

In particular embodiments, the distance between the filter and the magnets is between 1 mm and 40 mm, preferably between 2 mm and 20 mm.

In particular embodiments, the filter is a filter cylinder having a cylindrical shape, the microfiltration or ultrafiltration membrane being disposed on the mantle of the filter cylinder, the filtrate being collected through the center of the filter cylinder.

In particular embodiments, the assembly further comprises a first and a second container positioned around said filter cylinder. The filter cylinder is capable of moving around its axis such that the membrane alternatingly contacts said first and said second container. The filter cylinder comprises a divider running parallel to its axis, the divider dividing the filter cylinder in a filtration section and a particle harvesting section. The filtration section is arranged for ensuring an under pressure under the filtration membrane in said filtration section relative to the first container. The particle harvesting section is arranged for ensuring a pressure under the filtration membrane in said particle harvesting section which is equal to or greater than the pressure in said second container. The anti-fouling device is positioned in the second container such that it contacts the part of said membrane in said second container.

In particular embodiments, the magnetisable particles comprise a ferromagnetic material. Optionally, the magnetisable particles are spheroidal particles. In particular embodiments, the magnetisable particles have a size between 35 and 350 µm, preferably between 50 and 150 µm.

In particular embodiments the magnetisable particles have a magnetisation between 25 and 250 emu/g, preferably between 50 and 100 emu/g. Further provided is the use of a device comprising one or more magnets and a plurality of magnetisable particles for cleaning a microfiltration or ultrafiltration membrane.

Further provided is a method for filtering micro- and/or nanoparticles from a liquid suspension. The method comprises the following steps: contacting the suspension with a particulate material separation assembly provided herein. The particulate material separation assembly comprises an anti-fouling device and a filter membrane. A relative under pressure is maintained under the membrane with respect to the suspension to ensure filtration of the suspension through the filter membrane. A magnetic field is applied to the plurality of magnetisable particles of said anti-fouling device by means of the one or more magnets. This results in the formation of a magnetic brush. The method further involves the step of ensuring movement of said anti-fouling device, or a part thereof, and/or said filter membrane thereby cleaning the filter by means of said magnetic brush.

As an alternative to applying a relative under pressure under the filter membrane with respect to the suspension, the underside of the membrane may be contacted by a capillary material, i.e. a material capable of exerting high capillary forces on the fluid in the suspension. In some embodiments, the capillary material may be a textile belt which is passed along the filter membrane, and which is dried at a different position. Preferably, drying the textile belt is done by means of mechanical pressure, i.e. by squeezing be textile belt.

The method is preferably applied to micro algae.

DESCRIPTION OF THE FIGURES

The following description of the figures of specific embodiments of the invention is only given by way of example and is not intended to limit the present explanation, its application or use. In the drawings, identical reference numerals refer to the same or similar parts and features.

Figure 1:
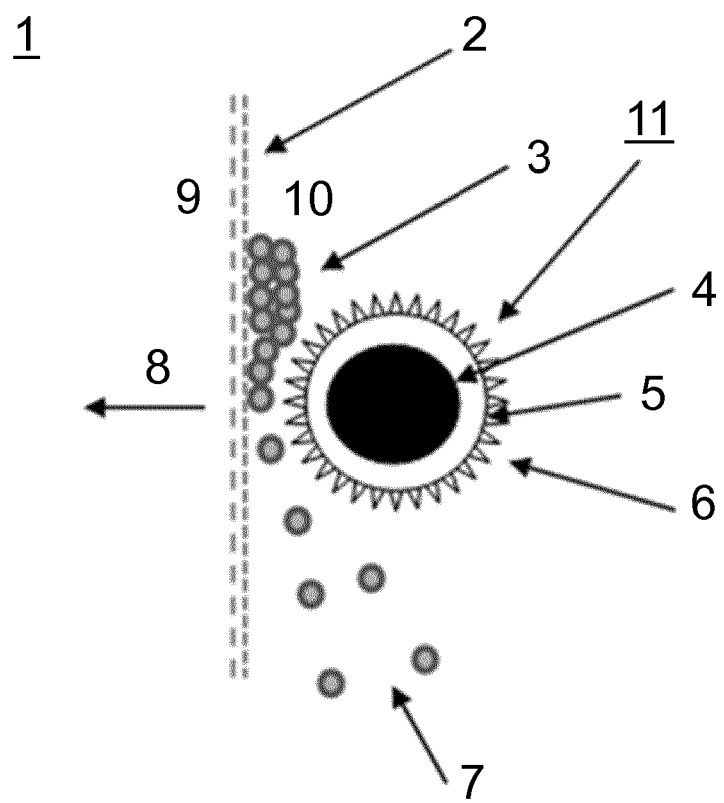
FIG. 1 shows a particular particulate material separation assembly according to an embodiment of the invention (1).

The following reference numerals are used in the description and figures:

1—particulate material separation assembly; 2—filtration membrane; 3—particulate material deposit; 4—(first inner) hull; 5—second outer hull; 6—dynamic bristles; 7—dislodged particles; 8—filtrate movement indicator; 9—low pressure zone; 10—high pressure zone; 11—antifouling device; 12—high particulate density container; 13—low particulate density container; 14—magnetic seal; 15—filter rotation indicator; 16—fluid evacuation indicator; 17—filter cylinder; 18—divider; 19—microfiltration membrane; 20—support beam; 21—magnets; 22—augmented magnetic field; 23—cancelled magnetic field; 24 Halbach array; 25—suspension movement indicator; 26—membrane support; 27—hull; 28—magnet movement indicator; 29—dynamic bristle movement indicator.

DESCRIPTION OF THE INVENTION

As used below in this text, the singular forms "a", "an", "the" include both the singular and the plural, unless the context clearly indicates otherwise.

The terms "comprise", "comprises" as used below are synonymous with "including", "include" or "contain", "contains" and are inclusive or open and do not exclude additional unmentioned parts, elements or method steps. Where this description refers to a product or process which "comprises" specific features, parts or steps, this refers to the possibility that other features, parts or steps may also be present, but may also refer to embodiments which only contain the listed features, parts or steps. The enumeration of numeric values by means of ranges of figures comprises all values and fractions in these ranges, as well as the cited end points.

The term "approximately" as used when referring to a measurable value, such as a parameter, an amount, a time period, and the like, is intended to include variations of +/−10% or less, preferably +/−5% or less, more preferably +/−1% or less, and still more preferably +/−0.1% or less, of and from the specified value, in so far as the variations apply to the invention disclosed herein. It should be understood that the value to which the term "approximately" refers per se has also been disclosed.

All references cited in this description are hereby deemed to be incorporated in their entirety by way of reference.

Unless defined otherwise, all terms disclosed in the invention, including technical and scientific terms, have the meaning which a person skilled in the art usually gives them. For further guidance, definitions are included to further explain terms which are used in the description of the invention.

The present invention relates to filtration devices and methods, in particular to devices and methods involving means for counteracting filter fouling during filtration. The presently disclosed devices and methods are useful in the context of processes for separating microscopic particles from a suspension. In particular, filtration is used. Generally, the driving force for filtration is a pressure difference. Also, filters used typically have a smooth solid filter medium having a small pore opening of 0.01 to 10 μm.

A solid filter medium is considered to be smooth when its surface has a surface roughness smaller than five times the size of the particulate material to be filtered. More preferably the surface roughness is smaller than two times the size of the material to be filtered, and even more preferably the surface roughness does not exceed the size of the particulate material to be filtered off.

Polymer membranes are particularly suitable solid filter media in the context of the present disclosure. However, other solid filter media can be used as well. Suitable solid filter media include: ceramic membranes, sintered metal membranes, woven membranes, and non-woven membranes.

Figure 3:
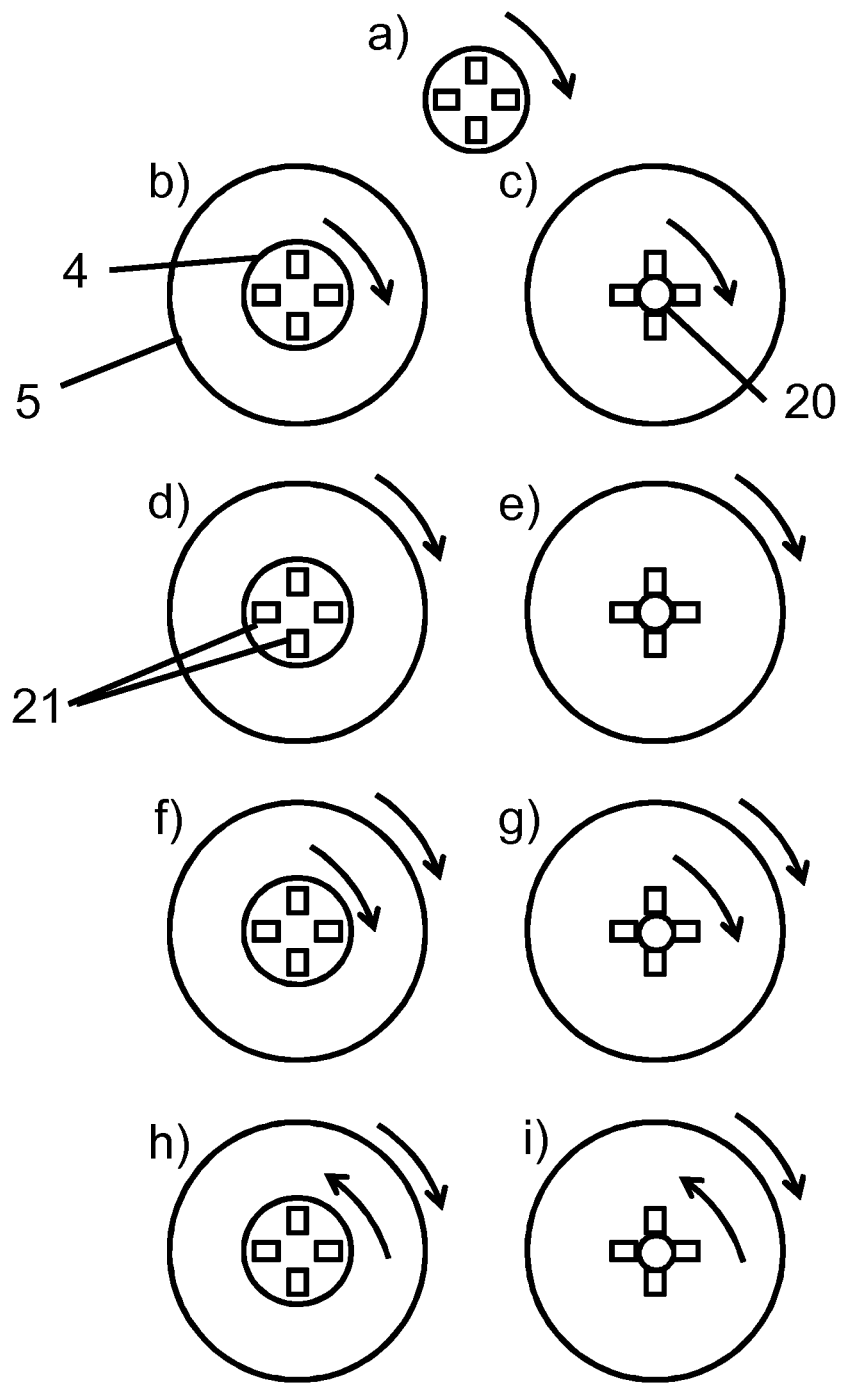
FIG. 3 shows a number of alternative antifouling device (11) configurations according to embodiments of the invention.

According to the present invention, a magnetic brush is used for removing filter cake from filtration membranes. The magnetic brush comprises magnets and oblong features which are subjected to the magnetic field generated by said magnets. In the devices provided herein the filter and the antifouling device are arranged to be moveable with respect to each other such that the oblong features are capable of brushing against the filtration membrane. It will be understood that that the entire antifouling device does not necessarily have to be moveable as a whole with respect to the filtration membrane. In particular embodiments, only part of the antifouling device is moveable with respect to the filtration membrane. Examples of such embodiments are shown in FIG. 3 and in the corresponding example.

The "hairs" of the magnetic brush, i.e. the oblong features, can be either fixed or move freely within the magnetic field. One type of suitable magnetic brush is a magnetorheological brush, such as described, for example, in Xiao Huang et. al. (Soft Matter, 2014, 10, 1537-1543). In particular embodiments, the hairs of the brush move freely within the magnetic field generating a "virtual" brush for removing filter cake from the filter. Preferably, filter cake is removed continually during use, but it can be envisaged that the brush is applied in between uses of the filter. The soft, virtual brush is created by means of one or more magnets which create a magnetic field, and a plurality of magnetisable particles.

In particular, magnetisable particles self-assemble into dynamic bristles, also named hair-like structures, under influence of a magnetic field. The dynamic bristles as referred to herein thus relate to the alignment of particles along the magnetic field lines extending from the pole of a magnet. Indeed, the assembly of the present invention is characterized by the fact that during use, the magnetisable particles are maintained in their configuration as dynamic bristles in the vicinity of the magnets. Aligned magnetic particles are used in copying devices and printers for applying powder to electrostatic images without stripes. Surprisingly, it appears that such structures can be used for cleaning filters, for example in the context of microfiltration-based micro algae harvesting.

The following description explains the present invention in terms of antifouling devices comprising one or magnets and a plurality of magnetisable particles which self-assemble into dynamic bristles under influence of the magnets' magnetic field. However, it will be appreciated that the dynamic bristles can be readily replaced by the magnetorheological bristles described in Soft Matter, 2014, 10, 1537-1543. Accordingly, provided herein is a particulate material separation assembly, i.e. a device for separating particles from a suspension comprising a fluid and particles. It comprises a filter and an anti-fouling device. The filter comprises a filtration membrane, preferably a microfiltration or an ultrafiltration membrane. The antifouling device comprises one or more magnets and a plurality of magnetisable particles. The filter and/or at least a part of the antifouling device are arranged to be moveable with respect to each other. Typical distances between the one or more magnets and the filtration membrane are 1 to 40 mm, preferably 1 to 30 mm, more preferably 2 to 20 mm.

During normal operation, the magnets give rise to a magnetic field, and the magnetisable particles interact with the magnetic field such that the magnetisable particles are arranged in a plurality of dynamic bristles. In other words, the magnetisable particles self-assemble into dynamic bristles under influence of the magnetic field. Accordingly, a brush comprising the one or more magnets and the plurality of magnetisable particles is formed by bringing the magnetisable particles in the magnetic field of the magnets. The properties of the brush can be adapted by means of the strength of the magnetic field, and by adapting the quantity of magnetisable particles. The properties of the dynamic bristles can be adapted by means of the strength of the magnetic field, the spatial distribution of the magnetic field, the magnetisability of the magnetisable particles, and the size of the magnetisable particles.

Magnetic brush formation can be done in a separate brush forming unit or can be done in situ in the filtration assembly. One method for forming a magnetic brush comprises bringing a metered amount of magnetisable particles into contact with the surface of the antifouling device. The dynamic bristles will then self-assemble due to the presence of the magnetic field lines. In one embodiment, the metered amount of magnetisable particles is delivered from a continuous powder bed of the magnetisable particles by a scraping blade.

Figure 11:
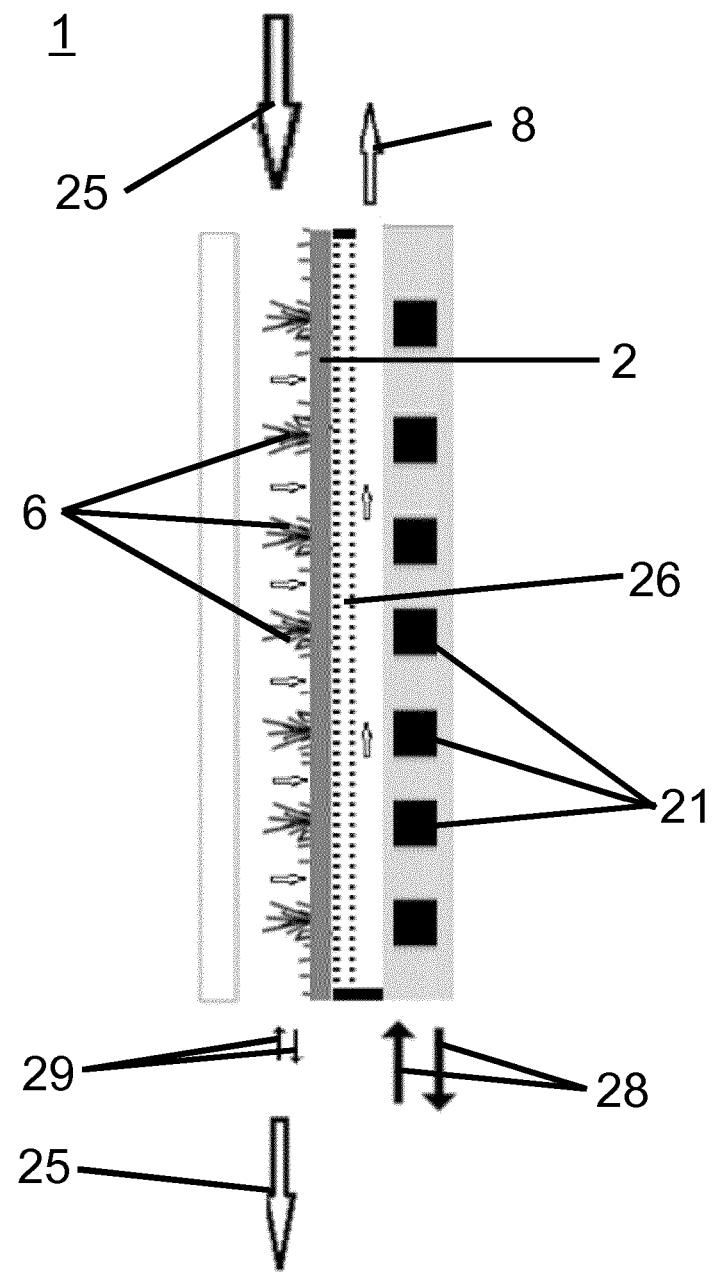
FIG. 11 shows a particular particulate material separation assembly according to an embodiment of the invention (1).

In alternative embodiments, the magnetic brush is formed from magnetisable particles at the suspension-facing side of the filter membrane and magnets at the underside of the membrane. Note that the terms "filter membrane" and "filtration membrane" as used herein can be used interchangeably. The membrane's underside is the side facing away from the suspension. An exemplary embodiment of such a configuration is shown in FIG. 11, and it is discussed in example 12. During normal operation, the plurality of magnetisable particles are kept in place on the membrane under influence of the magnetic field emanated by the magnets, The magnets are operationally connected to a linear actuator for moving them back and forth in a direction substantially parallel to the membrane. Under influence of the changing magnetic field created by the moving magnets, the dynamic bristles move back and forth across the membrane's surface, thereby cleaning the membrane, and preventing the formation of particulate material deposits.

When the antifouling device is operated, the magnets are moved with respect to the filter membrane. As a result, the dynamic bristles move as well and consequently brush against the filtration membrane, thereby preventing excessive fouling of the membrane by dislodging particles from the membrane surface. Various types of relative movement between the antifouling device and the filtration membrane are possible. In one embodiment, the antifouling device is configured to move as a whole relative to the filter membrane and/or the filter membrane is moved with respect to the antifouling device. In another embodiment, the one or more magnets in the antifouling device are moved, under the influence of which the magnetisable particles move as well. Surface material parts of the antifouling device such as a first and/or second cylindrical hull (see below) are kept stationary. The surface material parts are present between the one or more magnets and the plurality of magnetisable particles. In yet another embodiment, the surface material parts are moved and the one or more magnets are kept stationary. In a further embodiment, both magnets and surface material are moved with respect to the filter membrane. At least some of these embodiments are explained in more detail later on in the present disclosure.

The present particulate material separation assembly offers a number of significant advantages: no chemicals are needed for filtration membrane cleaning, there is a low energy cost, and cleaning causes only a small mechanical impact. Indeed the "softness" of the anti-fouling device can be regulated by means of magnetic interactions which are explained in more detail below. In general terms, the softness can be modified by means of the strength of the magnetic field, the magnetic properties of the magnetisable particles, and on the size of the magnetic particles. Generally speaking, the smaller the particles, the lower the magnetization, and the lower the magnetic field strength, the softer the bristles. Softer bristles generally cause less membrane erosion. However, very soft bristles may lack strength and may be susceptible to relatively high losses of magnetisable particles during filtration membrane cleaning.

Another advantage is that wear of brush hairs does not occur because there are no actual brush hairs, but only virtual hairs, i.e. the dynamic bristles which are built from magnetic particles are dynamic structures which are constantly regenerated from the magnetic particles. If the magnetisable particles need to be replaced, they can be removed from the magnets. Optionally, released magnetisable particles are collected by means of one or more additional magnets that function as pick-up magnets. In some embodiments, the filtration assembly comprises a concentrate drain. In such embodiments, the one or more pick-up magnets are preferably placed at the concentrate drain.

It will be understood by the skilled person that particle size and shape and magnetic forces can be optimized depending on the set up and application. For example, in case a ceramic membrane is used, and in case the particles to be filtered are mechanically stable, a relatively stiff magnetic brush can be used. Without wishing to be bound by theory, it is generally believed that larger magnetisable particles and stronger magnetic fields result in stiffer magnetic brushes.

The antifouling device may have any of a number of suitable configurations, a number of which are detailed below.

In particular embodiments, the one or more magnets are rigidly connected to a support structure which allows simultaneous movement of different magnets. More preferably the support structure also prevents the magnets from being contacted with fluids during use, e.g. by encasing the magnets. The nature of the support structure is not critical to the invention and will be dependent on the nature of the set-up, more particularly the size of the membrane, etc. In particular embodiments the support structure is a box or a cylinder. Preferably, the support structure encases the magnets. Also, the support material preferably allows magnetic field lines to pass through. Accordingly, suitable support materials include materials with a relatively weak, or no magnetic response. In particular, suitable support materials include polymers, aluminium, and copper.

In particular configurations, the antifouling device comprises a support structure for the magnets which is a cylindrical hull. The one or more magnets are rigidly connected to the cylindrical hull and the cylindrical hull is coupled to a rotary actuator which allows rotating the cylindrical hull around its longitudinal axis. In particular embodiments, the magnets are positioned within the cylindrical hull and plurality of magnetisable particles is disposed outside of the cylindrical hull. During normal operation, the magnetic field created by the magnets inside the cylindrical hull extends outside of the cylindrical hull and the plurality of magnetisable particles self-assemble into dynamic bristles extending from the cylindrical hull under influence of the magnetic field of the one or more magnets.

Accordingly, the magnetisable particles and the cylindrical hull form a brush. By rotating the magnets disposed in the cylindrical hull, the dynamic bristles rotate as well. Optionally, the cylindrical hull rotates together with the magnets. By positioning the cylindrical hull sufficiently close to the filter, the dynamic bristles brush over the surface of the membrane when rotating on the cylindrical hull. The "rotation" of the antifouling device as described in this context need not be a full rotation around its axis, but can be back and forth movements around its axis. If additionally, the antifouling device and the filter are moved relatively to each other, the dynamic bristles gradually contact different areas of the filter, This allows a particularly elegant way of cleaning the filter.

In particular embodiments, the support structure encasing the magnets has a rough surface. This prevents sliding of the magnetisable particles on the support structure, which enhances filtration membrane cleaning efficiency.

In particular embodiments, the distance between the support structure and the filtration membrane is typically envisaged to be 1-2 mm. This is an efficient distance for filter cleaning. The distance of the magnets to the membrane will depend on the strength of the magnet. In particular embodiments, the magnets comprise neodymium. For neodymium magnets, it was found that a distance of 1 to 40 mm, preferably 2 to 20 mm between the magnets and the filtration membrane to be cleaned is suitable Other suitable materials, mixtures, and ceramics for building the magnets are mentioned in US2003015474. Suitable materials include iron, nickel, cobalt, cerium, praseodymium, neodymium, and samarium. Suitable mixtures include samarium cobalt, neodymium iron boron. In fact, any ceramic, or any other high coercivity material with high intrinsic coercivity may be used as well.

The impact of the brush on the filter can be regulated via the movement velocity of the dynamic bristles, higher movement velocity (such as higher rotational velocity in case of a cylindrical hull) generally corresponding to a higher impact. Typical relative velocities between the dynamic bristles and the filter membrane are between 0.05 and 20 cm/s, preferably between 0.1 to 10 cm/s. These relative surface velocities are found to be highly effective for filter membrane cleaning.

In particular embodiments, the support structure to which the magnets are rigidly attached is further encased by another "outer" structure which closely fits around the "inner" support structure. This has the advantage that the inner support structure is not contacted with any fluids and that the outer structure does not need to follow the movements of the magnets on the inner support structure. This will be exemplified by way of a support structure which is a cylindrical hull. For instance, in particular embodiments, the cylindrical hull to which the magnets are rigidly attached is a first cylindrical hull positioned within a second cylindrical hull. In particular embodiments, the first cylindrical hull is arranged to rotate during normal operation, and the second cylindrical hull is arranged to remain stationary during rotation of the first cylindrical hull. The plurality of magnetisable particles is disposed outside of the second cylindrical hull. They form dynamic bristles, at least some of which extend away from the second cylindrical hull under influence of the magnetic field generated by the magnets in the first cylindrical hull.

As detailed above, instead of a first cylindrical hull, any type of support structure or magnet positioning means may be used. In particular embodiments, the magnet support structure comprises a support beam to which the magnets are rigidly attached.

As detailed above, the support structure may move to ensure limited movement of the magnets while the second cylindrical hull remains stationary or moves the brush to other parts of the filter. The different configurations are illustrated in FIG. 3 when using a cylindrical hull. For instance, alternatively, the magnet positioning means remain stationary while the second cylindrical hull rotates. Another possibility is that both magnet positioning means and the second cylindrical hull rotate simultaneously, either in the same direction or in opposite directions.

One preferred embodiment includes rotating magnet fastening means and a stationary second cylindrical hull. Preferably, the magnet fastening means are a first inner cylindrical hull. These embodiments are particularly suited when the filtration assembly is used for filtering particles from a liquid medium: efficient liquid proof sealing can be made, and the internal rotating part and corresponding bearings can be effectively separated from the surrounding liquid medium In some embodiments, both the magnet fastening means and the second cylindrical hull both do not rotate about their axis. In these embodiments, relative motion between the antifouling device and the filtration membrane may be achieved in one of several ways. When the filter is provided as a flat panel, it may move in a linear translation with respect to the antifouling device, or equivalently, the antifouling device may move in a linear translation with respect to the filter. When the filter is cylindrical, the antifouling device may remain stationary, and the cylindrical filter may rotate about its axis.

Preferably, when using a cylindrical hull, the magnetic field created by the one or more magnets is cylindrically symmetrical. This makes mechanical design easier. Cylindrical symmetry can be achieved by aligning the magnetic dipole of the one or more magnets along a radial direction of the cylindrical hull. A radial direction is a direction in a plane perpendicular to the axis of the cylindrical hull which also intersects the axis of the cylindrical hull.

In particular embodiments, the support structures are provided as plastic casing encasing the magnets, for example a casing made of PMMA (Poly(methyl methacrylate)).

In order to ensure a magnetic field which extends over a surface (such as that of a cylindrical hull), typically multiple aligned magnets of the same size are used, such as at least 4, 5, 6, 7, 8, 9, 10 or more. In particular embodiments, the magnets are positioned such that their magnetic dipoles are aligned. In particular embodiments, the magnets can be circumferentially aligned around a central axis. Alternatively, the magnets can be positioned in a parallel array, in an alternating array, or in a Halbach array. In a parallel array, magnets are positioned in a line and their magnetic moments are aligned in the same direction. In an alternating array, the magnets are positioned in a line and the magnetic moments of adjacent magnets are opposite. Halbach arrays are discussed in detail below.

In particular embodiments, the magnets are circumferentially aligned around a central axis and the magnetic dipole of at least one magnet has a radial orientation opposite to that of the circumferentially adjacent magnets. In further particular embodiments, the magnetic dipole of every magnet has a radial orientation opposite to that of the circumferentially adjacent magnets. This arrangement results in thin, relatively compact bristle formation. In this configuration, the "hairs" (the dynamic bristles) of the brush extend from one magnet to the other, the density of hairs being low at the poles and high in between the adjacent poles.

The concept "radial orientation" refers to the relative position of the north and south pole of a magnet in a radial direction, with respect to the cylinder's axis. The expression "circumferentially adjacent magnets" refers to magnets which are adjacent on a plane perpendicular to the cylinder's axis.

In particular embodiments, the magnets are circumferentially aligned around a central axis and the magnetic dipole of one or more magnets has a radial orientation identical to that of circumferentially adjacent magnets. Preferably, the magnetic dipole of every magnet has a radial orientation identical to that of circumferentially adjacent magnets. This arrangement results in a thick, rather compact bristle formation, wherein the "hairs" are concentrated at the tops of the magnet poles.

In particular other embodiments, the support structure to which the magnets are rigidly attached is planar. In a similar way as discussed for the cylindrical embodiments, the planar support structure can encase the magnets or can be encased by another "outer" structure, or hull. Typically, the hull is closely positioned to the magnets.

In particular embodiments, the membrane is supported by a membrane support. The membrane support is positioned at the underside of the membrane and allows filtrate to pass through. The membrane support may be a porous material and/or it may have a structure comprising openings, such as a mesh- or grid-like structure. In particular embodiments, the membrane support comprises a magnetisable material and/or one or more permanent magnets. This allows obtaining a more directional and stiffer brush comprising dynamic bristles.

Figure 10:
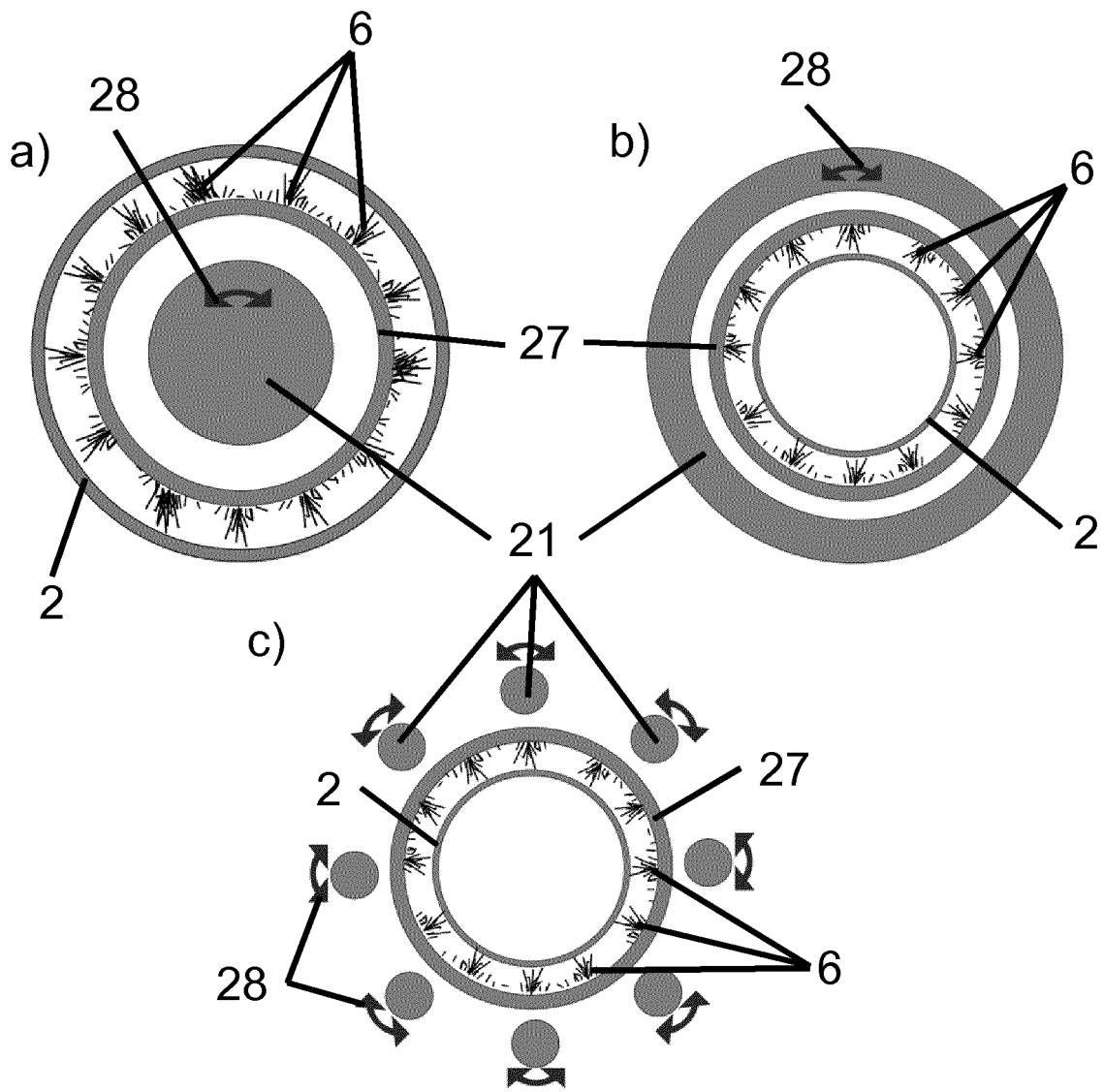
FIG. 10 shows a number of antifouling device configurations.

In particular embodiments, the particulate matter separation assembly comprises a cylindrical filtration membrane, and the antifouling device is disposed within the resulting filter cylinder. The antifouling device comprises cylindrically arranged magnets disposed within a cylindrical hull. The axes of the filter cylinder, the cylindrical hull, and the cylindrically arranged magnets are aligned. Dynamic bristles are disposed on the outer surface of the cylindrical hull. During normal operation, particle-bearing suspension is brought in a high pressure zone between the cylindrical hull and the filtration membrane. Outside the filtration membrane, a low pressure zone is maintained. Filtration through the membrane occurs under influence of the pressure difference between the high and low pressure zones. During normal operation, the cylindrically arranged magnets rotate about their axis, which gives rise to a changing magnetic field. The dynamic bristles move under influence of the changing magnetic field and brush against the filtration membrane, which cleans the membrane. An example of this configuration is shown in FIG. 10, panel a).

In particular embodiments, the particulate matter separation assembly comprises a cylindrical filtration membrane, and the antifouling device is disposed around the resulting filter cylinder. The antifouling device comprises cylindrically arranged magnets disposed around a cylindrical hull, and the cylindrical hull is disposed around the filtration membrane. The axes of the filter cylinder, the cylindrical hull, and the cylindrically arranged magnets are aligned. Dynamic bristles are disposed on the inner surface of the cylindrical hull. During normal operation, particle-bearing suspension is brought in a high pressure zone between the cylindrical hull and the filtration membrane. On the inside of the filtration membrane, a low pressure zone is maintained. Filtration through the membrane occurs under influence of the pressure difference between the high and low pressure zones. During normal operation, the cylindrically arranged magnets rotate about their axis, which gives rise to a changing magnetic field. The dynamic bristles move under influence of the changing magnetic field and brush against the filtration membrane, which cleans the membrane. An example of this configuration is shown in FIG. 10, panel b).

In particular embodiments, the particulate matter separation assembly comprises a cylindrical filtration membrane, and the antifouling device is disposed around the resulting filter cylinder. The antifouling device comprises a plurality of magnets arranged in a plurality of linear arrays which are cylindrically symmetrically disposed around a cylindrical hull. The cylindrical hull is positioned around a cylindrical filtration membrane. The axes of the filtration membrane and the hull coincide. Each linear array rotates about its longitudinal axis. On the inner surface of the hull, dynamic bristles are disposed. During normal operation, particle-bearing suspension is brought in a high pressure zone between the cylindrical hull and the filtration membrane. On the inside of the filtration membrane, a low pressure zone is maintained. Filtration through the membrane occurs under influence of the pressure difference between the high and low pressure zones. During normal operation, the dynamic bristles move under influence of the moving magnetic field created by the moving magnets. This causes the dynamic bristles to brush against the filtration membrane, thereby cleaning the filtration membrane in the process. An example of this configuration is shown in FIG. 10, panel c.

Figure 5:
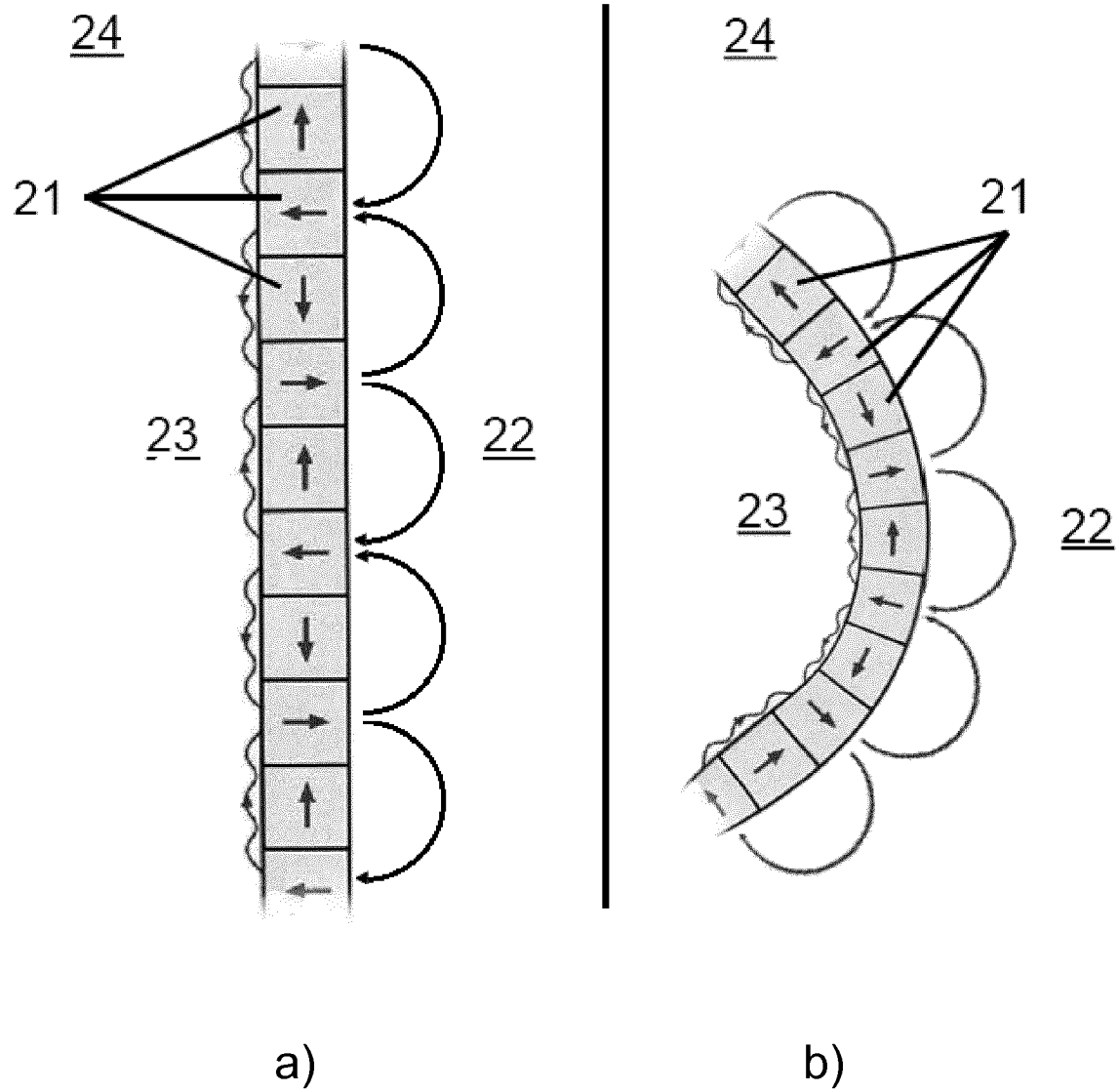
FIG. 5 shows a magnet configuration according to an embodiment of the invention.
Figure 9:
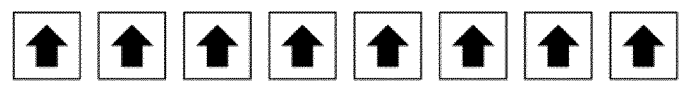
FIG. 9 shows a number of magnet configurations.
Figure 9:
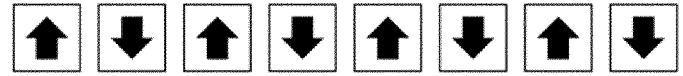
Figure 9:
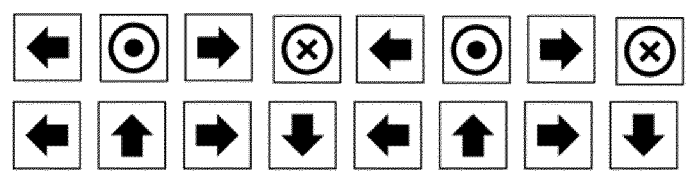
Figure 9:
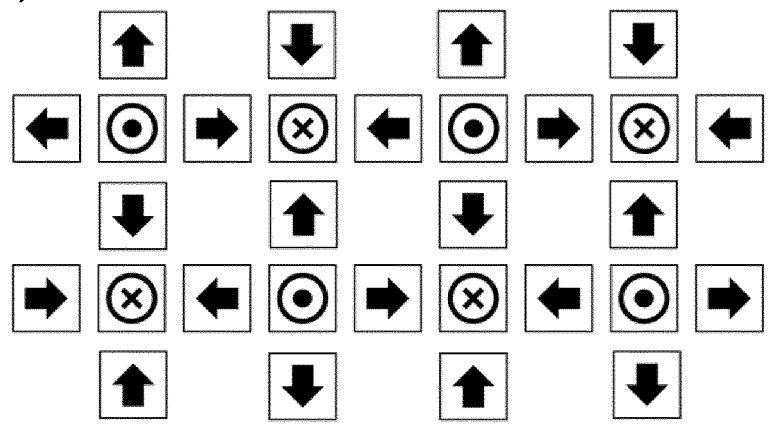

In particular embodiments, the antifouling device may comprise a Halbach array, which is an arrangement of magnets resulting in addition of magnetic field lines on one side of the array, thereby forming an augmented magnetic field at that side of the Halbach array. On the other side, the magnetic field lines cancel, thereby forming a cancelled magnetic field. Examples of Halbach arrays are shown in FIGS. 5 and 9. Halbach arrays are particularly useful for creating one-sided magnetic brushes: magnetisable particles preferentially self-assemble into dynamic bristles on the side with the augmented magnetic field. Halbach arrays can be configured in any one of a variety of ways. In particular embodiments, the Halbach array is a linear Halbach array (see e.g. FIG. 5, panel a) or FIG. 9, panel c). In other particular embodiments, the Halbach array is a curved Halbach array (see e.g. FIG. 5, panel b)). In other particular embodiments, the Halbach array is a planar Halbach array (see e.g. FIG. 9, panel d).

Halbach array-based antifouling devices may be combined with either planar or cylindrical filters. In case of planar filters, they are generally swept across the filter surface periodically. In case of cylindrical filters, the filter generally rotates about its axis and the antifouling device remains stationary.

In particular embodiments, the Halbach array is provided within a support structure as described above, More particularly, a support structure which encases the array shields it from certain external influences, such as particulate material-bearing suspensions.

In particular embodiments, the distance between the filter and the magnets is between 1 mm and 40 mm, preferably between 2 mm and 20 mm.

This allows efficient cleaning of the filtration membrane.

As stated before, the filter in the particulate material separation assembly provided herein may be cylindrical or planar. In case the filter has a cylindrical shape, the microfiltration or ultrafiltration membrane is preferably disposed on the mantle of the filter cylinder, and the filtrate is preferably collected through the center of the filter cylinder.

In particular embodiments, the filter is smooth and abrasion resistant. A smooth surface is defined as a surface with a surface roughness smaller than five times the size of the particulate material to be filtered. Preferably the surface roughness is smaller than two times the size of the material to be filtered, and more preferably the surface roughness does not exceed the size of the particulate material to be filtered. Examples of abrasion resistant filters are ceramic filter membranes and highly crosslinked polymer membranes and/or membranes with a glass transition temperature (Tg) above 25° C., more preferably above 50° C., even more preferably above 75° C.

In particular embodiments, the filter has a surface potential, i.e. an electrical double layer, which has the same polarity as the particles which are to be filtered from the suspension to be filtered. This results in electrostatic repulsion between the filtration membrane and particulate material deposits, which facilitates filter cleaning. Many micro algae have a negative surface potential. For filtering watery suspensions baring these micro algae, membranes having a negative surface charged, e.g. sulphonate group-bearing polymer membranes, are preferred.

In particular embodiments, the filtration membrane is hydrophobic. In case of filtration of aqueous suspensions, hydrophobic membranes are most resistant to fouling. The membrane pore size is preferably smaller than the particles to be filtered from the suspension. Suitable filtration membranes include sefar woven—open type, and Millipore mixed cellulose with a pore diameter around 0.45 µm.

As stated before, the filter may be cylindrical, i.e. it may be a filter cylinder. In particular embodiments, the filter cylinder comprises a perforated cylinder covered by a removable filtration membrane. Accordingly, the filtration membrane can be easily replaced when needed. The perforated cylinder may be formed of any of a variety materials. One suitable class of materials is stainless steel. When the perforated cylinder is formed of steel, or another ferromagnetic material, it influences the magnetic field generated by the magnets. The skilled person appreciates that due account of this influence should be taken when designing the magnetic field of the antifouling device.

It will be understood by the skilled person that the particulate material separation assembly provided herein can be used in a multitude of set ups. In particular embodiments, the filtration assembly comprises a first and a second container positioned around said filter cylinder. Also, the cylindrical filter further comprises a divider which divides the filter in a filtration section and a particle harvesting section. Preferably, the divider runs parallel to the filter cylinder's axis.

An example of a filtration set up is further described herein. The filtration section is disposed adjacent to the first container, and is separated from the first container by the filtration membrane. The filtration section is arranged for ensuring an under pressure under the membrane in said filtration section, relative to the pressure in the first container. The expression "under the membrane" refers to the side of the membrane inside the filter cylinder.

The particle harvesting section is disposed adjacent to the second container and is separated from the second container by the filtration membrane. The particle harvesting section is preferably arranged for ensuring that the pressure inside the particle harvesting section is equal to, or optionally higher than, the pressure in the second container. Generally, but not mandatorily, the second container is kept at atmospheric pressure.

The filter cylinder, or at least the filtration membrane, is capable of moving around its axis such that the membrane in said filtration section alternatively contacts said first and said second container. Note however, that the filtration section and the particle harvesting section remain stationary. In order to allow rotation while simultaneously allowing for fluid drainage, the filter is preferably provided with a rotary coupling. The rotary coupling may be fluidly connected to a fluid drain, or to a fluid collection container.

The anti-fouling device is positioned in the second container such that the dynamic bristles contact the part of the membrane in the second container. The under pressure in the filtration section allows for filtering particulate material-bearing suspensions whereas the higher pressure in the particle harvesting section allows for more efficient filter cleaning.

Preferably, the particulate matter concentration in the second container is measured.

In some embodiments, it may be measured by means of viscosity measurements, higher viscosities corresponding to higher micro particle concentrations. In some embodiments, the micro-particle concentration is measured by UV-VIS measurements, for example at a wavelength of 800 nm.

In particular embodiments, a pre-determined amount of suspension is removed from the second container when the particle concentration has exceeded a pre-determined threshold. The suspension in the second container is then replenished with more diluted suspension, preferably with suspension drawn from the feed of the filtration assembly. When the suspension is a micro algae suspension in water, the pre-determined threshold may be between 50 g/l and 100 g/l.

In an alternative embodiment, the filtration assembly only comprises one container and a planar filter. The filter comprises a low pressure zone at a pressure which is lower than the pressure in the container. Accordingly, the container is a high pressure zone. The low pressure zone and the high pressure zone are separated by a filtration membrane. The filtration membrane is continually cleaned by means of an anti-fouling device as described before. The anti-fouling device continually moves parallel to the filtration membrane to clean the membrane. Preferably, a stirrer is provided in the container for continually stirring the suspension, which aids homogenization of the suspension.

During normal operation, fresh suspension comprising particulate material is continually added which results in a continual increase of the algae concentration. After a certain period of time, the particulate matter concentration reaches a critical limit such that the effective filter time becomes unacceptably small. The critical limit of particulate matter concentration is preferably measured indirectly by means of the filtrate flow rate: when the filtrate flow rate drops below a pre-determined value, the critical limit of particulate matter concentration is considered to have been reached. The effective filter time is the time between filter obstruction by particulate material deposits and particulate deposit removal by means of the filter brush. When the critical limit is reached, the suspension is removed, fresh suspension is added to the vessel, and the process may be restarted.

A large variety of magnetisable particles may be used in the context of the present disclosure. Preferably, the magnetisable particles have a size between 10 µm and 1 mm, preferably between 25 μm and 250 μm: particles smaller than 10 μm might pose a health risk, while particles larger than 1 mm tend to form relatively hard dynamic bristles which my result in membrane damage. Suitable particle sizes for most applications are between 35 μm and 150 μm, for example 50 or 100 μm; wherein the particle sizes are reported as volume average particle sizes. Suitable materials include magnetic metals, magnetic metal oxides, and composite particles comprising a binder material and dispersed magnetisable materials. The binder material can be selected from the list comprising organic binders such as polymers, and inorganic binders such as ceramic materials. Suitable materials include manganese and magnetite. The magnetisable particles may be coated with a protective coating, for example a fluoropolymer, acrylic, or silicone coating. The coating can offer to the material a lower friction coefficient thus avoiding scratching of the membrane when it is brought in contact with the dynamic bristles. A preferred coating for lower friction coefficient is PTFE. A coating can also be applied to induce to the magnetisable particles a surface charge. For example by applying an acrylic acid containing butylacrylate—methylmethacrylate coating (molar ratio of acrylic acid:methylmethacrylate:butylacrylate: 1:30:69), a negative charge will arise on the particle surface, thus inducing a repulsion towards negatively charged particles, such as negatively charged microalgae. This will prevent the algae from sticking to the particle surface. Another feature that can be realised by the coating is a protection of the magnetisable material with respect to the liquid medium. This will for example be important in case iron particles would be used in a saline medium, which often used in micro algae cultivation. The thickness of the coating is preferably from 0.5 to 5 μm. In particular embodiments, the magnetisable particles comprise a ferromagnetic material. Additionally or alternatively, the magnetisable particles may comprise a ferrimagnetic or paramagnetic material.

Known ferrimagnetic materials include YIG (yttrium iron garnet), cubic ferrites composed of iron oxides and other elements such as aluminum, cobalt, nickel, manganese and zinc, hexagonal ferrites such as $PbFe_{12}O_{19}$ and $BaFe_{12}O_{19}$, and pyrrhotite, $Fe_{1-x}S$.

Ferromagnetic materials mostly comprise one or more metal ions, for example Co, Fe, Ni, MnBi, MnSb, Dy, although also metal oxide based ferromagnetic materials are known, such as CrO. Further examples of preferred magnetisable materials are $Fe_3O_4$, $MnO.Fe_2O_3$, $ZnO(0.5)CuO(0.5)Fe_2O_3$. Examples of preferred ferromagnetic materials are Fe, Ni, Nd.

In particular embodiments, the magnetisable particles comprise a composite material. The composite material comprises a binder resin and one or more magnetisable pigments. In one embodiment, such a composite material comprises between 70 and 80%, preferably 75% of magnetisable pigment, and between 20 and 30%, preferably 25% resin, wherein the percentages are weight percentages. The magnetisable pigment may comprise ferrimagnetic or ferromagnetic materials, preferably the ferrimagnetic or ferromagnetic materials listed above. Preferably, the magnetisable pigment has a particle size smaller than 1 μm. Suitable resins include polyesters, including bisphenol A-fumaric acid condensate.

In particular embodiments, the magnetisable particles are spheroidal particles.

In particular embodiments, the magnetisable particles are coated. This can help preventing degradation, e.g. oxidation, of the magnetisable material. Also, it can make the magnetisable particles smoother. Smoother magnetisable particles are desirable because they result in less membrane erosion.

In particular embodiments, the magnetisable particles have a size between 35 and 300 μm, preferably between 50 and 150 μm.

In particular embodiments the magnetisable particles have a magnetisation between 25 and 250 emu/g, more preferably between 50 and 100 emu/g.

In particular embodiments, the one or more magnets have a coercive field strength between 100 and 2700 kA/m and a residual magnetism between 0.4 and 1.5 T.

In particular embodiments, the magnetic field strength at the antifouling device's hull, i.e. at the interface between the antifouling device and the suspension, is between 10 and 25 mTesla, preferably between 15 and 20 mTesla.

Further provided is the use of a device comprising one or more magnets and a plurality of magnetisable particles for cleaning a filtration membrane, for example a microfiltration or ultrafiltration membrane. This results in surprisingly efficient cleaning of filtration membranes.

Further provided is a method for filtering micro- and/or nanoparticles from a suspension. The suspension may comprise, on the one hand, any gas or liquid and on the other hand micro and/or nanoparticles. In particular embodiments, the fluid in the suspension is a liquid. The present method is especially suitable for filtering micro algae from water. However, filtering other particles from other liquids is possible as well. For example, the present method is applicable to filtration of particulate matter from air. In this case, a sufficient air stream should be present for mobilizing the particles. Achieving a sufficient air stream is easier in dead end filtration compared to cross-flow filtration. Accordingly, when the present methods and devices are used for filtering particles in air, dead-end filtration is preferably used.

In a first step, the method involves contacting the suspension with a particulate material filtration assembly. The particulate material filtration assembly comprises an antifouling device and a filtration membrane and may have any configuration as previously described.

A relative under pressure is ensured under the membrane with respect to the suspension to ensure filtration of said suspension through said filter membrane. In this context, it is noted that a filtration membrane comprises one side in contact with the feed, and one side in contact with the filtrate. The expression "under the membrane" refers to the side of the membrane in contact with the filtrate.

As an alternative to applying a relative under pressure under the filter membrane with respect to the suspension, the underside of the membrane may be contacted by a capillary material, i.e. a material capable of exerting high capillary forces on the fluid in the suspension. In some embodiments, the capillary material may be a textile belt which is passed along the filter membrane, and which is dried at a different position. Preferably, drying the textile belt is done by means of mechanical pressure, i.e. by squeezing the textile belt.

The underside of the membrane refers to the side of the membrane in contact with the filtrate, or differently worded to the side opposite to the side at which the suspension is present, or yet differently worded to the side of the membrane to which fluid in the suspension is transported.

In a second step, the method involves applying a magnetic field to the plurality of magnetisable particles of said antifouling device by means of the one or more magnets. This causes the plurality of magnetisable particles to self-assemble intodynamic bristles Stated differently, the plurality of magnetisable particles forms the "bristles" of a magnetic brush.

The antifouling device, and particularly its dynamic bristles are then brought into contact with the filter membrane.

Finally, at least part of the anti-fouling device is moved with respect to the filter membrane, which causes cleaning of the filter by means of the magnetic brush.

The present methods and devices may be applied in a variety of industries such as biofuel production, food processing and/or pharmacy. In particular, the present methods and devices are especially well-suited for filtering micro algae from water. Accordingly, in particular embodiments, the algae are micro algae. In some embodiments, the micro algae are selected from the list comprising: *nanochloropsis, chlorella, hematococcus, Chlorella vulgaris, Haematococcus pluvialis*, and *Spirulina platensis*. One suitable algae strain is *Nannochloropsis* sp., strain CCAP211/78.

The present invention will be illustrated by the following non-limiting embodiments.

EXAMPLES

Example 1

In a first example, reference is made to FIG. 1 which shows a conceptual drawing of a particulate material separation assembly (1). It comprises a low pressure zone (9) and a high pressure zone (10) which are separated by a microfiltration membrane (2). The low pressure zone (9) is maintained at a lower pressure than the high pressure zone. Under the driving force of the pressure differential between the low pressure zone (9) and the high pressure zone (10), particulate material-bearing suspension is filtered: the fluid in the suspension passes through the membrane (2), from the high pressure zone (10) to the low pressure zone (9), which is indicated by means of a filtrate movement indicator (8). In the process, particles in the suspension are deposited on the filter (2), thereby forming a particulate material deposit (3). The particulate material deposit (3) forms a barrier against fluid flow through the membrane (2) and if left undisturbed, it would block fluid flow through the membrane altogether. Accordingly, the particulate material deposit (3) should be periodically removed from the membrane. This is achieved by means of an antifouling device (11) comprising a first inner hull (4), a second outer hull (5), and a plurality of dynamic bristles (6). The first inner hull (4) and the second outer hull (5) are both cylindrical.

The inner hull (4) houses a plurality of magnets. The magnetic dipole moments of these magnets are aligned along radial directions of the inner hull. The magnetic dipole moments of circumferentially adjacent magnets are opposite.

The first inner hull (4) is disposed within the second outer hull (5). The magnetic field emanating from the plurality of magnets in the first inner hull (4) penetrates the outer hull. Under its influence, magnetisable particles self-assemble into dynamic bristles (6) on the outer hull (5).

During normal operation, the antifouling device (11) is translated parallel to the filtration membrane (2), and the first inner hull (4) is made to rotate about its axis whereas the second outer hull (5) does not rotate about its axis. The distance between the second outer hull (5) and the filtration membrane (2) is between 2 and 5 mm, though distances between 2 and 20 mm are workable as well.

Under influence of the rotational movement of the first inner hull (4), the magnetic field outside of the second outer hull (5) rotates as well. Under the influence of the rotating magnetic field, the magnetisable particles in the dynamic bristles (6) are rearranged, and consequently, the dynamic bristles (6) move over the outer surface of the second outer hull (5). Combined with the translational movement of the antifouling device (11), this results in removal of particulate material deposits (3) on the filtration membrane (2). The removed particulate material is returned into the suspension in the high pressure zone (10), which is indicated by the dislodged particles (7) shown in FIG. 1.

Example 2

Figure 2:
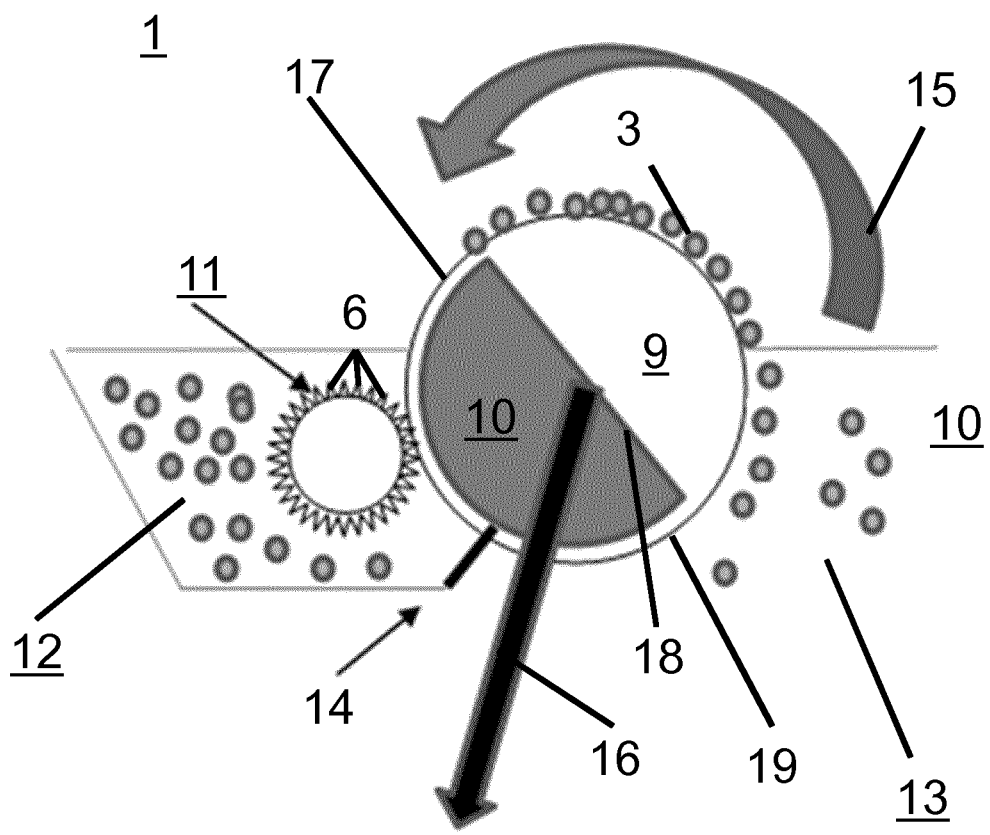
FIG. 2 shows a particulate material separation assembly according to an embodiment of the invention (1).

In a second example, reference is made to FIG. 2 which shows a conceptual drawing of a particulate material separation assembly (1). It comprises a high particle density container (12) and a low particle density container (13). Both containers (12,13) are filled with a water-micro algae suspension. The micro algae concentration in the high particle density container (12) is higher than in the low particle density container (13). Between the high particle density container (12) and the low particle density container (13), a filter cylinder (17) is disposed, the mantle of which comprises a microfiltration membrane. The filter cylinder (17) is divided in two compartments by a divider (18) running parallel to the axis of the filter cylinder (17). The first compartment is a high pressure zone (10), which is generally kept at atmospheric pressure. The second compartment is a low pressure zone (9) which is kept at a pressure lower than the pressure in the high pressure zone (10). The filter cylinder (17) continually rotates. However, the divider (18) remains stationary.

The high particle density container (12) and the low particle density container (13) are high pressure zones (10), and generally operate at atmospheric pressure. The second compartment of the filter cylinder (17) is separated from the low particle density container (13) by the filter cylinder's (17) microfiltration membrane. Water in the low particle density container (13) is transported through the microfiltration membrane due to the pressure differential between the second compartment of the filter cylinder (17) and the low particle density container (13), and it is evacuated which is schematically shown by a fluid evacuation indicator (16). Micro algae suspended in the water are swept along by the resulting flow and are deposited on the microfiltration membrane (19), thereby forming a particulate material deposit (3). Should the particulate material deposit (3) be allowed to build up for an extended period of time, it would block the water flow from the low particle density container (13) to the second compartment of the filter cylinder (17). In order to prevent this build up, the filter cylinder (17) is made to rotate about its axis in a counter-clockwise fashion, as indicated by a filter rotation indicator (15). The particulate material deposit (3) adheres to the filter's microfiltration membrane (19), and it is transported to the high particulate density container (12). In the high particulate density container (12), an antifouling device (11) is positioned adjacent to the filter cylinder (17), i.e. at a distance of 0.5 to 2.0 mm from the filter cylinder (17). The antifouling device operates as explained in Example 1. Due to the cleaning action of the antifouling device (11), micro algae in the particulate material deposit (3) are dislodged from the microfiltration membrane (19), and are released into the high particle density container (12). Cleaning is further aided by the high pressure zone (10) inside the first compartment of the filter cylinder (17): the higher pressure in the high pressure zone (10) compared to the low pressure zone (9) results in lower adhesion between the particulate material deposit and the microfiltration membrane (19). The cleaned microfiltration membrane is returned to the low particle density container (13) through continual rotation of the filter cylinder (17). A magnetic seal (14) between the high particulate density container (12) and the low particulate density container (13) prevents or minimizes mixing between the contents of these two containers. In the low particulate density container (13), the microfiltration membrane is brought in contact with the water-micro algae suspension, and the filtration cycle starts over.

It should be noted that whereas the aforementioned process has been described as a sequence of steps, it occurs as a continuous process in reality. Also, under normal operating conditions, some or all of the above steps occur simultaneously.

During normal operation, the micro algae concentration in the high particulate density container (12) gradually increases. It is monitored by means of viscosity measurements, higher viscosity corresponding to higher micro algae concentration. When the viscosity has reached a pre-determined level, a pre-determined amount of concentrated micro algae suspension is removed and fresh micro algae suspension with low micro algae suspension is added to the high particulate density container (12). Alternatively, the micro algae concentration in the high particulate density container (12) may be measured by means of UV-VIS spectroscopy at a wavelength of 800 nm. The following empirical relation can be used: D800=1.7922+0.3658*ln (particle concentration in g/l), wherein R2=98.55%, with R2 the square of the sample correlation coefficient, and with D800 optical density at 800 nm.

The particulate material separation assembly (1) further has the following detailed characteristics: Mechanical drive, including bearings, of the anti-fouling device (11) and the filter cylinder (17) is provided in a separate dry compartment. The drive mechanisms do not come in contact with the suspension. The width of the low particle density container and the high particle density container is 1.200 m. The length of the anti-fouling device and the filter cylinder is 1.000 m. The height of the low particle density container (13) is 1 m. The height of the high particle density container (12) is 0.200 m. The filtration cylinder (17) has a diameter of 0.220 m. It is formed as a perforated tube covered by the microfiltration membrane (19). The microfiltration membrane (19) is a spare part consumable. The filter cylinder (17) is provided with a rotary coupling at one side for draining liquids by means of under pressure. The rotary coupling is connected to a cyclone or a barrel which is positioned on the frame, under the container. The barrel is connected to a vacuum pump. The barrel is also provided by a number measuring instruments: liquid level measurement and a manometer. The barrel also serves as a buffer for filtered liquids.

Example 3

In a third example, a number of alternative anti-fouling device configurations are discussed.

In configuration a) the antifouling device comprises one hull (4) enclosing a plurality of magnets (21). The hull (4) and magnets (21) rotate during cleaning.

In configurations b), d), f), and h), the antifouling device comprises a first inner hull (4) enclosing a plurality of magnets (21) and a second outer hull (5). The magnets (21) are rigidly attached to the first inner hull (4). During cleaning, the first inner hull (4) and/or the second outer hull (5) rotate. In particular: in configuration b), the first inner hull (4) rotates whereas the second outer hull (5) remains stationary; in configuration d), the first inner hull (4) rotates whereas the second outer hull (5) rotates; in configuration f), the first inner hull (4) and the second outer hull (5) rotate in the same direction; and in configuration h), the first inner hull (4) and the second outer hull (5) rotate in opposite directions.

In configurations b), d), f), and h), the antifouling device comprises a support beam (20) to which the magnets (21) are rigidly attached. The antifouling device further comprises a second outer hull (5) which encloses support beam (20) and the magnets (21). During cleaning, the support beam (20) and/or the second outer hull (5) rotate. In particular: in configuration c), the support beam (20) rotates whereas the second outer hull (5) remains stationary; in configuration e), the support beam (20) remains stationary whereas the second outer hull (5) rotates; in configuration g), the support beam (20) and the second outer hull (5) rotate in the same direction; in configuration i), the support beam (20) and the second outer hull (5) rotate in opposite directions.

Example 4

Figure 4:
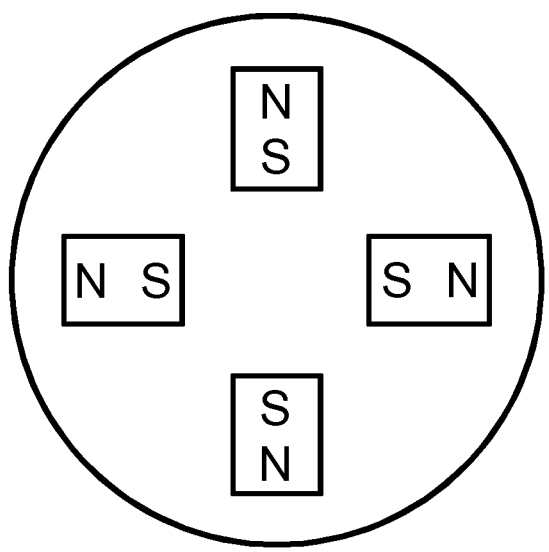
FIG. 4 shows two alternative magnet configurations.
Figure 4:
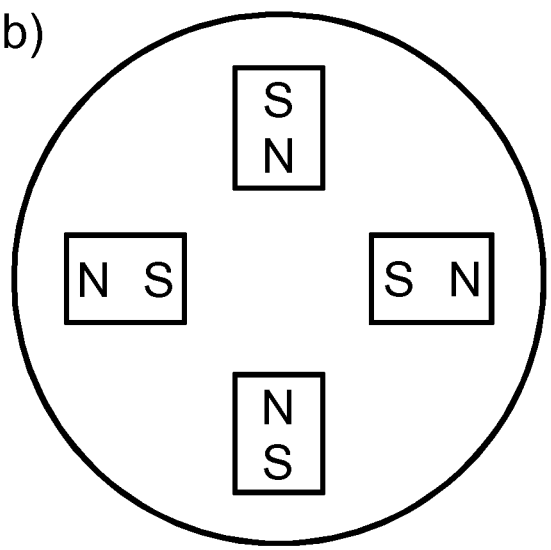

In a fourth example, reference is made to FIG. 4 in which two alternative magnet configurations are shown. In this example, the magnets are shown inside a cylindrical hull, but the configurations are readily extendible to structures in which the magnets are attached to a support beam.

In both panels a) and b), the magnet's magnetic dipole moments are aligned along radial directions. However, the radial orientation of the magnets is different in panels a) and b): in panel a), the radial orientation of the magnetic dipole moment is identical for all magnets, whereas in panel b), the radial orientation of the magnetic dipole moment of circumferentially adjacent magnets is opposite.

Example 5

In a fifth example, reference is made to FIG. 5 in which yet another magnet configuration is shown, namely a Halbach array (24). In particular, panel a) shows a linear Halbach array, and panel b) shows a curved Halbach array. Linear Halbach arrays can be used for example for cleaning planar filter membranes. Curved Halbach arrays can be used for example for cleaning curved filter membranes, such as cylindrical filter membranes.

Halbach arrays as such are known in the art. They comprise a plurality of magnets (21), the magnetic dipole moments are arranged as indicated by the arrows in FIG. 5. This particular configuration of magnetic dipole moments results in the addition of magnetic field lines on one side of the array, thereby forming an augmented magnetic field (22) at that side of the Halbach array (24). On the other side, the magnetic field lines cancel, thereby forming a cancelled magnetic field (23).

In the context of the present disclosure, they may be used for generating a magnetic field in anti-fouling devices. They are particularly useful for creating one-sided magnetic brushes: magnetisable particles preferentially self-assemble into dynamic bristles on the side with the augmented magnetic field (22), thereby creating a one-sided magnetic brush. Such a configuration is particularly advantageous when the anti-fouling device does not rotate during cleaning, and simply moves parallel to the filtration membrane. In this case, the anti-fouling device is arranged such that the augmented magnetic field (22) faces the filtration membrane, and, in presence of magnetisable particles, dynamic bristles self-assemble between the Halbach array and the filtration membrane.

Example 6

In a sixth example, reference is made to a specific set of experiments. In particular, the experiments involve the use of a particulate material separation assembly according to example 1. A magnet construct with Nd magnets alternatingly positioned on an axis, was rotated with a speed of 30 rpm in a hull of PMMA with diameter of 25 mm. The magnetic field strength at the surface of the second outer hull was 18 mTesla. The gap between the hull and the membrane was 2 mm. The magnetisable particles were Mn-ferrite particles having a magnetisation of 80 emu/g, and having a particle size of 100 μm. The membranes used were 0.45 μm Millipore Cellulose microfiltration membranes. The experiments show that the cleaning of the anti-fouling device is clearly visible. Cross flow speeds of 0.2 m/s are found to be suitable. The energy used to activate the anti-fouling device was 15.5 W. The membranes were inspected with a compound light microscope. No membrane damage was visible after testing continuously for 4 hours.

Example 7

Figure 6:
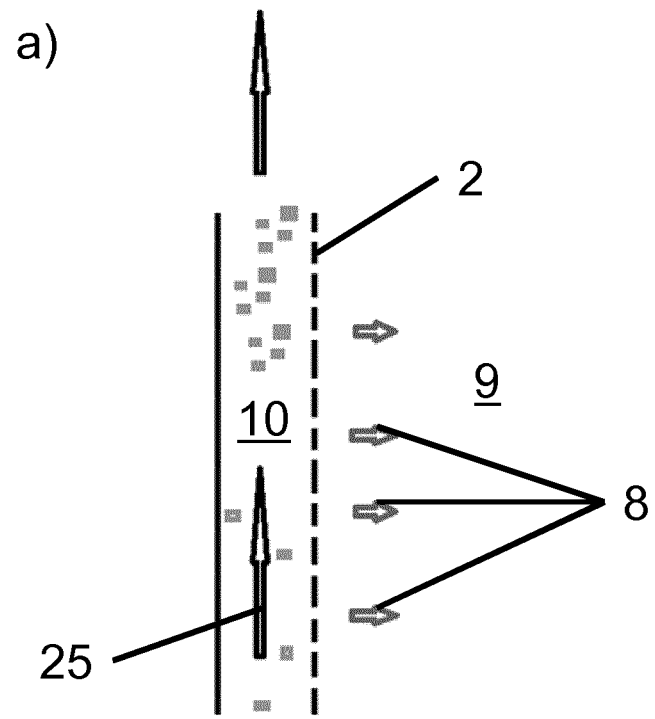
FIG. 6 shows two flow configurations in which the present particulate material separation assemblies may be used.
Figure 6:
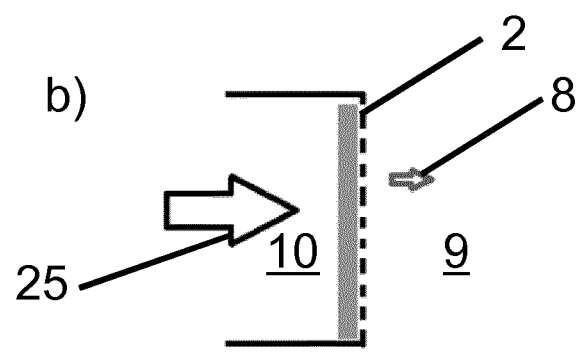

In a further example, reference is made to FIG. 6. FIG. 6 shows two flow configurations in which the present particulate material separation assemblies may be used. In both configurations, continuous membrane cleaning is needed to prevent filtration membrane (2) clogging by particulate material deposits. In both configurations, suspension moves through a high pressure zone (10), as indicated by a suspension movement indicator (25). At the far side of a filtration membrane (2), a low pressure zone (9) is maintained. The pressure in the low pressure zone (9) is lower than that in the high pressure zone (10). Under the driving force of the pressure difference between the low pressure zone (9) and the high pressure zone (10), fluid moves from the high pressure zone (10) to the low pressure zone (9), as indicated by a filtrate movement indicator (8). Panel a) shows a cross-flow configuration, in which suspension moves parallel to the filtration membrane (2) Panel b) shows a dead end configuration in which suspension moves in a direction perpendicular to a filtration membrane (2), which is also indicated by a suspension movement indicator (25).

Example 8

Figure 7:
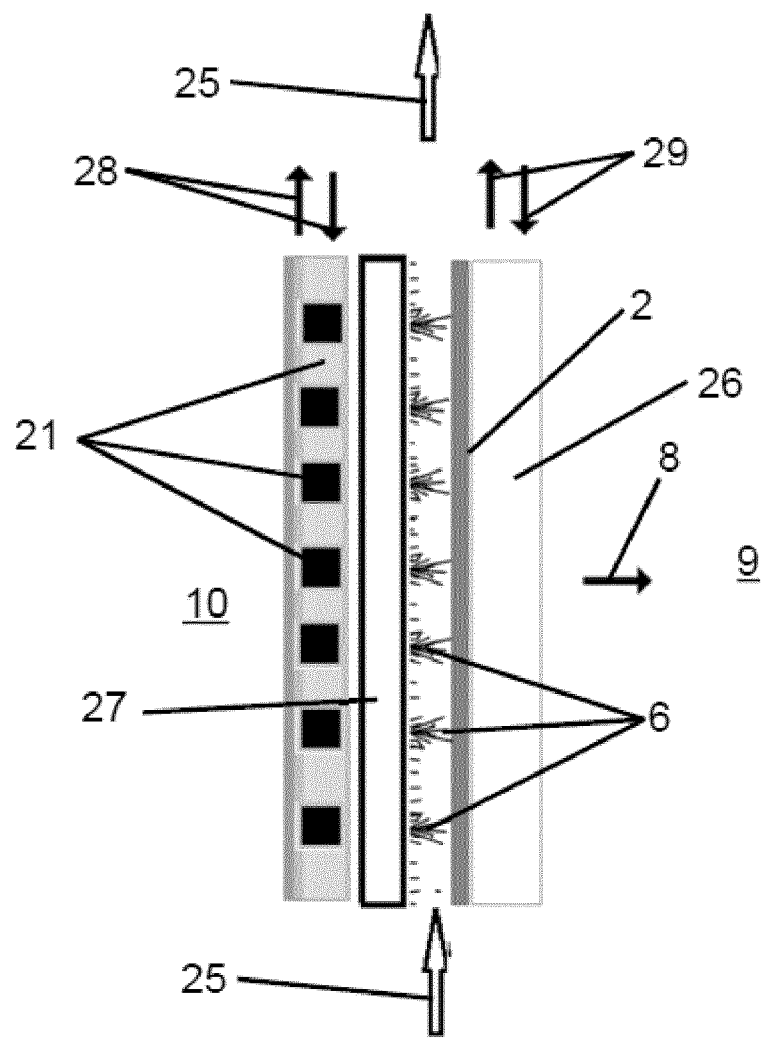
FIG. 7 shows a cross section of a particulate material filtration assembly according to an embodiment of the invention.
Figure 8:
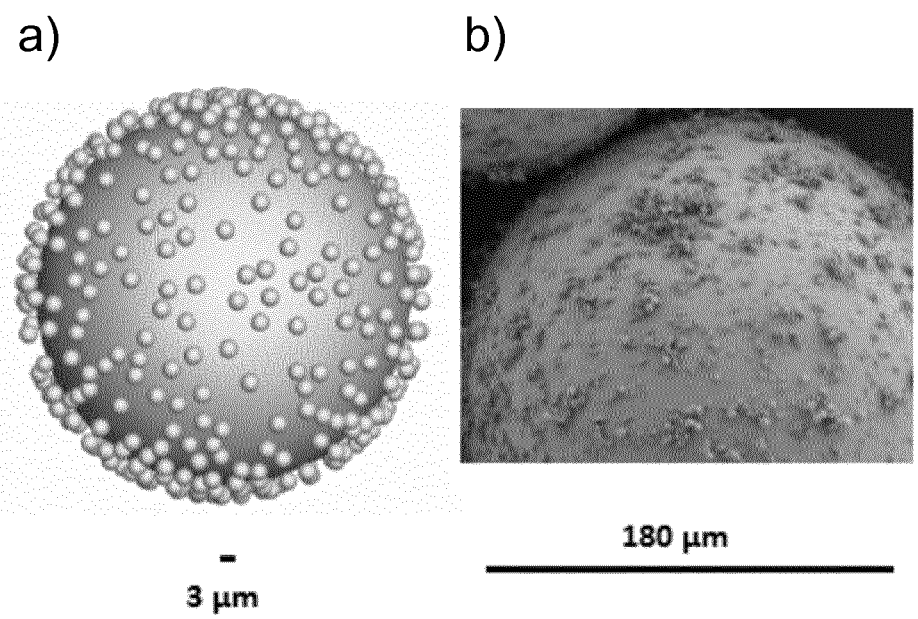
FIG. 8 shows a schematic representation (panel a) and a micrograph (b) of micro algae and magnetisable particles. The magnetisable particles are larger than the micro algae.

In a further example, reference is made to FIG. 7. FIG. 7 shows a cross section of a particulate material filtration assembly as provided herein. It comprises a filtration membrane (2) which has two sides. At one side, a high pressure zone (10) is maintained, and at the other side a low pressure zone (9) is maintained. The pressure in the low pressure zone (9) is lower than that in the high pressure zone (10). At the low pressure side (9), the membrane is supported by a membrane support (26). At the high pressure side, suspension flows along the membrane in a cross-flow configuration, as indicated by a suspension movement indicator. Also, the gas or liquid component of the suspension is drawn through the membrane under influence of the pressure differential between the high pressure zone (10) and the low pressure zone (9). The liquid or gas content in the suspension passes through the filtration membrane (2) and is removed, as indicated by a filtrate movement indicator (8). The particles in the suspension are arrested by the filtration membrane (2) and would cause membrane clogging by formation of particulate material deposits should they be left unperturbed. In order to prevent membrane clogging, an anti-fouling device is provided at the membrane's high-pressure side. The anti-fouling device comprises magnets (21) arranged in a Halbach array, a hull (27), and dynamic bristles (6). The hull (27) separates the magnets (21) from the suspension. It may enclose the magnets (21). The dynamic bristles (6) are formed of magnetisable particles which self-assembled on the hull (27) under influence of the magnetic field emanating from the magnets (21). The magnets (21) move with respect to the filtration membrane (2). The moving magnets create a moving magnetic field. Even though the hull remains stationary, the dynamic bristles (6) move under influence of this moving magnetic field, and the dynamic bristles (6) brush against the filtration membrane (2). Through this brushing action, particles are removed from the filtration membrane (2), thereby preventing the formation of particulate material deposits.

Example 9

In a further example, reference is made to FIG. 9 which shows a number of magnet configurations which are usable in antifouling devices, and in particular in flat antifouling devices. Panel a) shows a parallel array. In a parallel array, the magnetic moments of all magnets are aligned. Panel b) shows an alternating array. In an alternating array, the magnetic moments of adjacent magnets are opposite. Panel c) shows a linear Halbach array, in which the magnetic moments of the constituent magnets are arranged to create one side with an augmented magnetic field, and one side with a cancelled magnetic field. The top row shows the orientation of the magnetic moments of the magnets on the top of the Halbach array, and the bottom row shows the orientation of the magnetic moments of the magnets on the front of the Halbach array. Panel d) shows a planar Halbach array, one side of which features an augmented magnetic field, and the other side of which features a cancelled magnetic field.

A specific planar, or 2D, Halbach array according to panel d) is discussed in more detail now. The 2D Halbach array was constructed with Nd magnets (cubic with size 5 mm and magnetization grade N50), in a 5 mm milled PMMA plate, sandwiched between 2 plates of 1.5 mm PMMA. The 2D Halbach array was placed on top of a 5 mm PMMA plate, forming the dynamic brush with ferrite powder (MF100, PowderTech Japan) below the plate. A membrane, covered with a wet filter cake of Nanochloropsis was placed 2 mm below the brush. When moving the 2D Halbach array laterally, the dynamic brush managed to sweep away the filter cake. No lateral feed flow was used.

Example 10

In a further example, reference is made to FIG. 10 which schematically shows three configurations of a particulate material separation assembly. The particulate material separation assembly comprises a stationary filtration membrane (2), and an antifouling device comprising moving magnets (21) and a stationary hull (27).

Panel a) shows a configuration in which rotatably arranged magnets (21) are disposed within a stationary hull (27). The rotational movement of the magnets is indicated by means of a magnet movement indicator (28). Around the hull (27), a filtration membrane (2) is arranged. The magnets (21), the hull (21), and the filtration membrane (2) are all cylindrical and their axes are aligned. Even though the hull (21) remains stationary, the dynamic bristles (6) move under the influence of the moving magnetic field created by the rotating magnets. While moving, the dynamic bristles (6) brush against the filtration membrane (2), thereby cleaning the filtration membrane (2).

Panel b) shows a configuration in which magnets (21) are arranged in a cylinder mantle around a cylindrical hull (27). A cylindrical filtration membrane (2) is disposed within the hull (27). The axes of the magnets (21), the hull (27), and the filtration membrane (2) are aligned. The cylindrical hull (27) remains stationary whereas the magnets (21) rotate about their axis, as indicated by means of a magnet movement indicator (28). Dynamic bristles (6) disposed on the inner surface of the hull (27) move under influence of the moving magnetic field created by the moving magnets. This causes the dynamic bristles (6) to brush against the filtration membrane (2), thereby cleaning the filtration membrane in the process.

Panel c) shows a configuration in which magnets (21) are arranged in eight linear arrays. Each of the linear arrays rotates about its axis, as indicated by eight magnet movement indicators (28). The linear arrays are cylindrically symmetrically positioned around a cylindrical hull (27), which in turn is positioned around a cylindrical filtration membrane (2). The axes of the filtration membrane (2) and the hull (27) coincide. On the inner surface of the hull (27), dynamic bristles (6) are disposed. The dynamic bristles (6) move under influence of the moving magnetic field created by the moving magnets (21). This causes the dynamic bristles (6) to brush against the filtration membrane (2), thereby cleaning the filtration membrane in the process.

Example 11

In a further example, reference is made to a particulate matter separation assembly arranged as a crossflow filtration cell which was adapted to accommodate for a magnetic antifouling device with diameter of 25 mm on the feed (high pressure) side of the membrane. The antifouling device was mounted perpendicular to the direction of flow of the feed, forcing all the feed to pass through a gap of 2 mm between the hull of the antifouling device and the membrane. A magnet construction with Nd magnets alternatingly positioned on an axis was rotated with speeds of 25 to 50 rpm in a hull of PMMA with diameter of 25 mm. The gap between the hull and the membrane was 2 mm. The membranes used were 0.45 μm Millipore Cellulose microfiltration membranes. The experiments show that the cleaning of the anti-fouling device is clearly visible. Cross flow speeds of 0.2 m/s are found to be suitable, whereas for just avoiding algae sedimentation without use of the antifouling device a flow of at least 2 m/s was needed.

Example 12

In a further example, reference is made to FIG. 11. FIG. 11 shows a particulate material separation assembly (1) in cross-flow configuration. It features an alternative arrangement of magnets (21) and dynamic bristles (6). A particle-bearing suspension flows from along a membrane (2) as indicated by suspension movement indicators (25). The membrane is supported by a porous membrane support (26). Magnets (21) are positioned at the underside of the membrane (2) whereas dynamic bristles (6) are positioned on the suspension-facing side of the membrane (2).

The dynamic bristles (6) are formed from a plurality of magnetisable particles and are kept in place under influence of the magnetic field emanated by the magnets (21). During normal operation, the magnets (21) move back and forth, as indicated by magnet movement indicators (28). As a result, the dynamic bristles (6) move back and forth across the membrane's (2) surface, thereby cleaning the membrane (2), and preventing the formation of particulate material deposits. Thanks to the dynamic bristles' (6) cleaning action, fluid from the particulate-bearing suspension can pass through the membrane unobstructed, and the resulting filtrate is removed, as indicated by a filtrate movement indicator (8).

Example 13

Figure 12:
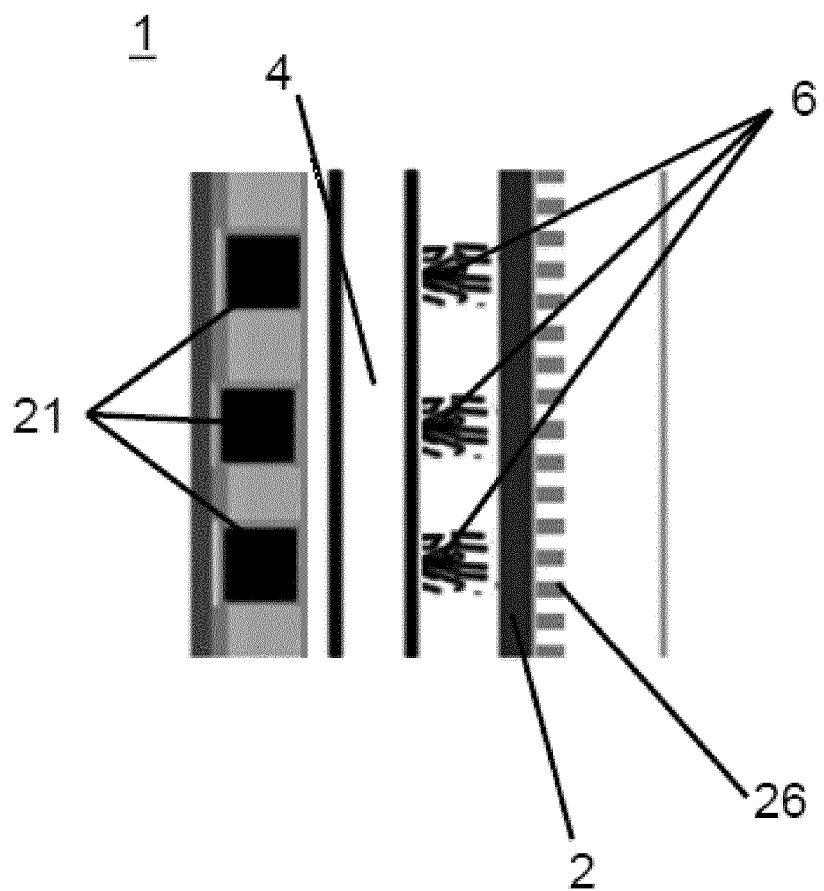
FIG. 12 shows a particulate material separation assembly (1) in which the antifouling device's magnets (21) and magnetisable particles are situated at the suspension-facing side of the filtration membrane (2).

In a further example, reference is made to FIG. 12. FIG. 12 shows a particulate material separation assembly (1) in which the antifouling device's magnets (21) and magnetisable particles are situated at the suspension-facing side of the filtration membrane (2). The magnets (21) are separated from the suspension by a hull (4). The magnetisable particles are situated between the hull (4) and the filtration membrane (2) and are arranged in dynamic bristles (6) under influence of the magnetic field. A magnetisable porous membrane support (26) is positioned at the underside of the filtration membrane (2). The porous magnetisable membrane support (2) allows obtaining a more directional and stiffer brush, the brush comprising the dynamic bristles (6).

Without wishing to be bound by theory, this effect on the brush is believed to be caused by a two-pronged effect of the magnetisable porous membrane support (26) on the magnetic field emanated by the magnets (21): first, the magnetisable porous membrane support (26) intensifies the magnetic field emanated by the magnets (21) and second, the magnetisable porous membrane support (26) renders the magnetic field more directional.

The invention claimed is:

1. A particulate material separation assembly (1) comprising:
   a filter comprising a filtration membrane (2); and
   an antifouling device (11) comprising a magnetic brush comprising one or more magnets (21) and a plurality of magnetisable particles,
   wherein the plurality of magnetisable particles are arranged in a plurality of dynamic bristles (6), said plurality of dynamic bristles being the bristles of said magnetic brush; and
   wherein the filter and at least a part of the antifouling device (11) are arranged to be moveable with respect to each other such that the dynamic bristles (6) are capable of brushing against the filtration membrane (2).

2. The particulate material separation assembly (1) according to claim 1 wherein the antifouling device (11) comprises a cylindrical hull, wherein the one or more magnets are fixed within the cylindrical hull, wherein the cylindrical hull is coupled to a rotary actuator for rotating the cylindrical hull around the cylindrical hull's longitudinal axis, and wherein the plurality of magnetisable particles are disposed outside of the cylindrical hull.

3. The particulate material separation assembly according to claim 2, wherein the cylindrical hull is a first cylindrical hull (4) positioned within a second cylindrical hull (5) which is arranged to remain stationary during rotation of the first cylindrical hull (4), and said plurality of magnetisable particles are disposed outside of the second cylindrical hull (5).

4. The particulate material separation assembly (1) according to claim 2, wherein the one or more magnets (21) have a magnetic dipole moment which is aligned along a radial direction of the cylindrical hull.

5. The particulate material separation assembly according to claim wherein said one or more magnets (21) are a plurality of magnets that are circumferentially aligned around a central axis, wherein the magnetic dipole moment of one magnet of said plurality of magnets has a radial orientation opposite to that of other magnets circumferentially adjacent to said one magnet.

6. The particulate material separation assembly according to claim wherein the one or more magnets (21) are a plurality of magnets that are circumferentially aligned around a central axis, wherein the magnetic dipole moment of one magnet of said plurality of magnets has a radial orientation identical to that of other magnets circumferentially adjacent to said one magnet.

7. The particulate material separation assembly according to claim 1 wherein the one or more magnets comprise at least four magnets, and in which the at least four magnets are arranged in a Halbach array.

8. The particulate material separation assembly (1) according to claim 1, wherein the distance between the filter and the magnets is between 1 mm and 40 mm.

9. The particulate material separation assembly (1) according to claim 1, comprising a mantle, wherein the filter is a filter cylinder having a cylindrical shape, and wherein the filtration membrane is a microfiltration or ultrafiltration membrane disposed on the mantle of the filter cylinder (17), the filtrate being collected through the center of the filter cylinder (17).

10. The particulate material separation assembly according to claim 9, which is further characterized in that
the assembly further comprises a first and a second container positioned around said filter cylinder whereby the filter cylinder is capable of moving around the filter cylinder's axis such that the membrane alternatingly contacts said first and said second container;
the filter cylinder comprises a divider running parallel to the filter cylinder's axis, the divider dividing the filter cylinder into a filtration section and a particle harvesting section; the filtration section being arranged for ensuring an under pressure under the filtration membrane in said filtration section relative to the first container; the particle harvesting section being arranged for ensuring a pressure under the filtration membrane in said particle harvesting section which is equal to or greater than the pressure in said second container;
the anti-fouling device is positioned in said second container such that it contacts the part of said membrane in said second container.

11. The particulate material separation assembly according to claim 1, wherein the magnetisable particles comprise a ferromagnetic material.

12. The particulate material separation assembly according to claim 1, wherein the magnetisable particles have a size between 35 and 350 µm.

13. The particulate material separation assembly according to claim 1, wherein the magnetisable particles have a magnetisation between 25 and 250 emu/g.

14. A method for filtering micro- and/or nanoparticles from a liquid suspension comprising:
contacting the suspension with a particulate material separation assembly according to claim 1 comprising said anti-fouling device and said filter comprising said filtration membrane;
ensuring a relative under pressure under said filtration membrane with respect to the suspension, or contacting the underside of the filtration membrane with a capillary material, to ensure filtration of said suspension through said filtration membrane;
applying a magnetic field to the plurality of magnetisable particles of said anti-fouling device by means of the one or more magnets, thereby forming said magnetic brush;
ensuring movement of said anti-fouling device and/or said filtration membrane thereby cleaning the filter by means of said magnetic brush.

15. The method according to claim 14, wherein the micro- and/or nanoparticles are micro algae.

16. The particulate material separation assembly according to claim 5, wherein the magnetic dipole moment of each magnet of said plurality of magnets has a radial orientation opposite to that of all circumferentially adjacent magnets.

17. The particulate material separation assembly according to claim 6, wherein the magnetic dipole moment of each magnet of the plurality of magnets has a radial orientation identical to that of all circumferentially adjacent magnets.

18. The particulate material separation assembly according to claim 1, wherein the magnetisable particles are spheroidal particles.

19. The particulate material separation assembly according to claim 1, wherein the magnetisable particles have a size between 50 and 150 µm and/or have a magnetisation between 50 and 100 emu/g.

* * * * *